United States Patent [19]

Hauske

[11] Patent Number: 4,857,641

[45] Date of Patent: Aug. 15, 1989

[54] C.12 MODIFIED ERYTHROMYCIN A DERIVATIVES

[75] Inventor: James R. Hauske, East Lyme, Conn.

[73] Assignee: Pfizer Inc., New York, N.Y.

[21] Appl. No.: 85,446

[22] Filed: Aug. 14, 1987

[51] Int. Cl.$^4$ ............................................. C07H 17/08
[52] U.S. Cl. ........................................ 536/7.3; 536/7.2
[58] Field of Search ................................... 536/7.2, 7.3

[56] References Cited

U.S. PATENT DOCUMENTS 3,864,347  2/1975  Gutzwiller et al. ............ 260/287 R
4,672,056  6/1987  Fernandes et al. ................... 536/7.2
4,686,207  8/1987  Freiberg et al. ....................... 514/29

OTHER PUBLICATIONS

Morrison et al., *Organic Chemistry*, 3rd Ed., 1979, p. 166.
Hauske et al., J. Org. Chem., vol. 48, pp. 5138-5140 (1983).

*Primary Examiner*—Johnnie R. Brown
*Assistant Examiner*—Elli Peselev
*Attorney, Agent, or Firm*—Peter C. Richardson; J. Trevor Lumb; Robert K. Blackwood

[57] ABSTRACT

Antibacterial 12,12'-anhydro-9R-hydroxy-9-deoxoerythromycin A derivatives, intermediate therefor and process of 12,12'-dehydration.

10 Claims, No Drawings

C.12 MODIFIED ERYTHROMYCIN A DERIVATIVES

BACKGROUND OF THE INVENTION

The present invention is directed to antibacterial 12,12'-anhydro-9R-hydroxy-9-deoxoerythromycin derivatives, having the formula (3) below, to intermediates therefor, having the formula (4) below, and to a selective process of dehydration (e.g. 4→3a, below).

Although the chemistry of the erythromycin series of antibiotics has been extensively studied for many years, and numerous antibacterial derivatives have been reported from these studies, there remains a demand for specialized derivatives, for example those having activity against erythromycin resistant strains, a wider spectrum of activity, or, as in the present case, a narrower spectrum of activity which permits topical use without significant potential for the development of resistant strains over the broader antibacterial spectrum.

Previously reported has been the conversion of erythromycin A (1) to the thiocarbonate (2):

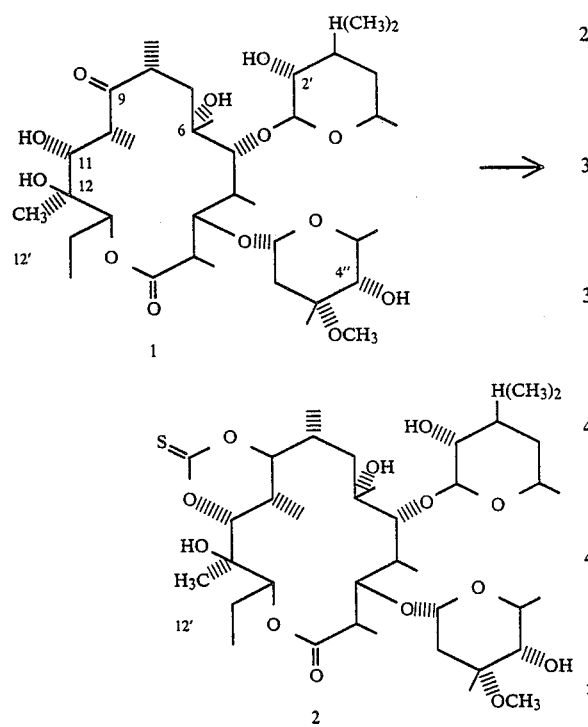

Hauske et al., J. Org. Chem., vol. 48, pp. 5138–5140 (1983). There, the compound (2) was named as a 9,11-cyclic-thionocarbonate erythromycin A. More systematically, following the "IUPAC Nomenclature of Organic Chemistry, 1979 Edition," Pergammon Press, particularly pp. 494–512, the compound (2) is alternatively named 9-deoxo-11-deoxy-9R,11-(thiocarbonyldioxy) erythromycin A or 9-deoxo-9R-hydroxy-9,11O,O-thiocarbonylerythromycin A. The compound (2) previously found use in the synthesis of C.9-modified erythromycin derivatives (Hauske et al., loc. cit.).

SUMMARY OF THE INVENTION

We have now found that the intermediate (2) possesses further utility as an intermediate for the synthesis of antibacterial C.12 modified erythromycin A derivatives, in particular compounds of the absolute stereochemical formula

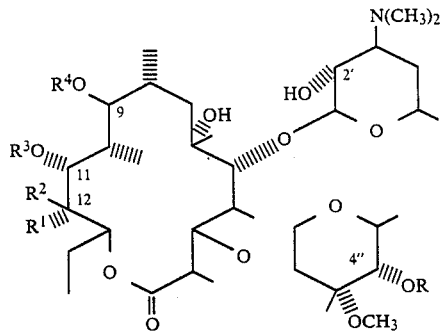

wherein
R is hydrogen or $(C_2-C_4)$alkanoyl;
$R^1$ and $R^2$ are taken separately, $R^1$ is hydroxymethyl and $R^2$ is hydroxy; or
$R^1$ and $R^2$ are taken together and are methylene ($CH_2=$); and
$R^3$ and $R^4$ are taken together and are thiocarbonyl ($>C=S$), with the proviso that when $R^3$ and $R^4$ are so taken, R is other than hydrogen;
or a pharmaceutically acceptable acid addition salt thereof.

Because of their ease of preparation and there antibacterial activity, the compounds (3) which are of particular value are as follows:

$R = CH_3CO; R^1 + R^2 = CH_2; R^3 + R^4 = CS;$  3a $R = CH_3CO; R^1 + R^2 = CH_2; R^3 = R^4 = $ hydrogen;  3b $R = R^3 = R^4 = H; R^1 + R^2 = CH_2;$  3c $R = CH_3CO; R^1 = HOCH_2; R^2 = OH, R^3 = R^4 = H;$  3d and $R = R^3 = R^4 = H; R^1 = HOCH_2, R^2 = OH.$  3e The key intermediate compound in the preparation of the compounds of the formula (3) is the compound of the absolute stereochemical formula

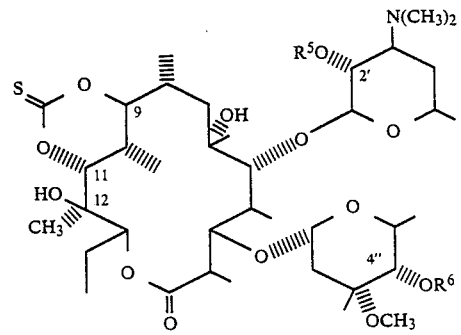

wherein
$R^5$ is $(C_2-C_4)$ alkanoyl or benzoyl; and
$R^6$ is $(C_2-C_4)$alkanoyl.

Compounds of the formula (4) which are of particular value are:

$R^5 = R^6 = CH_3CO;$ and  4a

-continued
$R^5 = C_6H_5CO; R^6 = CH_3CO.$  4b

A key process step in the present invention is the unexpectedly selective formation of the exocyclic double bond at the C.12-position in the dehydration step (e.g. 4a→3a), where exocyclic dehydration at the C.6-position, or 11,12-, 12,13-, 5,6- or 6,7-endocyclic dehydration appear as likely. Although in hindsight the formation of the exocyclic double bond isomer at C.12 may well be rationalized on the basis of steric considerations, it is difficult to rationalize a priori the selectivity observed between the C-12 and C-6 sites. However, determination of the solid state structure of a closely related analog, namely the 2'-benzoate of the compound (2) by X-ray methods (carried out by Gayle Shulte, Chemical Instrumentation Center, Yale University) permitted some insight into this phenomenon. Thus, calculation of the distance to neighboring centers, and measurement of the local molecular volume for the C.6 and C.12 centers, supports the notion that the C.12 position has somewhat reduced steric demand.

DETAILED DESCRIPTION OF THE INVENTION

The present invention is readily carried out, using transformations typified by the following scheme:

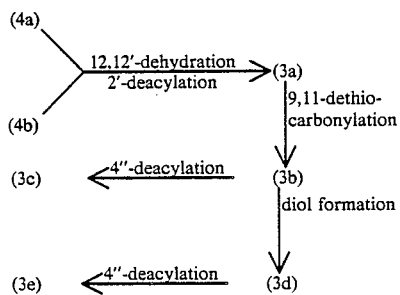

The starting diesters (4) are prepared from the known thiocarbonate (2) by conventional esterification methods as exemplified by the Preparations detailed below. When mixed esters are desired, selective 2'-acylation is initially accomplished by use of substantially one molar equivalent of the acylating reagent (e.g. anhydride or acid chloride). Further selective acylation at 4" (or at 2' and 4" when both groups are the same) is readily accomplished even with excess of the acylating agent, so long as forcing conditions (e.g., elevated temperature) are avoided.

Selective 12,12'-dehydration, with concommitant 2'-deacylation, of a compound of the formula (4) is readily accomplished by the action of at least one molar equivalent of thionyl chloride, usually in some molar excess (e.g. a total of 1.2 to 1.7 molar equivalents) in the presence of a molar excess of a tertiary amine (e.g., triethylamine) in a reaction-inert solvent (e.g. ethyl acetate). While temperature is not critical, somewhat reduced temperatures (e.g. about −20° to 25° C.) are preferred in order to minimize undesirable side reactions.

As used herein, the expression "reaction-inert solvent" refers to a solvent which does not interact with starting materials, reagents, intermediates or products in a manner which adversely affects the yield of the desired product.

Selective removal of the cyclic thiocarbonate ester (e.g., 3a→3b) is readily accomplished by means of sodium borohydride reduction in a reaction-inert, usually alcoholic solvent such as isopropanol. Temperature is not critical, e.g., the range of about 0–50° C. being generally satisfactory. Ambient temperatures are most convenient and avoid unnecessary heating or cooling. Any resulting borate complexes are readily hydrolyzed, e.g., by refluxing in methanol.

Stereoselective 12,12'-diol formation (e.g., 3b→3d) is readily accomplished by oxidation with an oxidant which is directed by steric control, thus selectively delivering oxygen from the less hindered beta-face, i.e., from above when the compounds are as herein depicted. An oxidant which meets these criteria and is otherwise well-suited for the purpose is osmium tetroxide in combination with sodium metaperiodate, which is employed in a reaction-inert solvent such as aqueous tetrahydrofuran/t-butyl alcohol. Temperature is not critical, e.g., the range of about 0–50° C. being generally satisfactory, and ambient temperatures most convenient and generally less costly.

The hydrolysis of 4"-alkanoate esters (e.g., 3b→3c; 3d→3e), or concurrent hydrolysis of 4"-alkanoate and 9,11-thiocarbonate (e.g., 3a→3c) is generally accomplished by base catalyzed hydrolysis using an excess of a base such as $NH_4OH$ or LiOH in an aqueous but otherwise reaction-inert solvent, such as aqueous methanol or aqueous dioxane. Temperature is not critical, the range of about 0–50° C. being generally satisfactory, and ambient temperatures most convenient and generally less costly.

The compounds of the formula (3) are tested for in vitro antibacterial activity by standard methods in which the minimum inhibitory concentrations (MIC's) in mcg/ml against one or more microorganisms is measured. One such procedure is the one recommended by the International Collaborative Study on Antibiotic Sensitivity Testing (Ericcson and Sherris, *Acta. Pathologica et Microbiologia Scandinav*, Supp. 217, Section B: 64–68 [1971]), and employs brain heart infusion (BHI) agar and an inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye. Like other polycyclic ether antibiotics, the present compound of the formula (I) typically shows Gram positive antibacterial activity, as illustrated in Table (I).

TABLE I

| IN VITRO ANTIBACTERIAL ACTIVITY OF COMPOUNDS OF THE FORMULA (3) | | | | |
|---|---|---|---|---|
| | | MIC, mcg/ml | | |
| Organism | Compound[a]: | 3a | 3b | 3d |
| Staph. aureus | 005 | 50 | >50 | >50 |
| | 052 | 50 | >50 | >50 |
| | 110 | 50 | >50 | >50 |
| Staph. epid. | 111 | 12.5 | >50 | >50 |
| Strep. faec. | 006 | 50 | >50 | 25 |
| Strep. pyog. | 054 | 50 | >50 | >50 |
| | 203 | 3.12 | 3.12 | 3.12 |

TABLE I-continued
IN VITRO ANTIBACTERIAL ACTIVITY OF COMPOUNDS OF THE FORMULA (3)

| Organism | Compound[a]: | MIC, mcg/ml | | |
|---|---|---|---|---|
| | | 3a | 3b | 3d |
| Strep. pneum. | 012 | 3.12 | — | — |
| E. coli | 470 | 6.25 | 25 | 12.5 |
| Pat. mult. | 001 | 25 | 25 | 50 |
| Neis. sic. | 000 | 50 | 50 | >50 |
| Hem. infl. | 038 | >50 | 50 | >50 |
| | 042 | 50 | >50 | 50 |
| | 012 | >50 | 50 | >50 |
| | 073 | 50 | >50 | 50 |
| | 078 | 50 | >50 | >50 |
| | 081 | 50 | >50 | >50 |

Although generally finding use as industrial disinfectants, the present compounds of the formula (3) are primarily useful as topical antibacterial agents, effective against superficial infections due to susceptible bacteria. These compounds are generally administered ad libitum as solutions, suspensions or solid blends containing about 0.1 to 2% w/w or w/v of the active ingredient in a pharmaceutically acceptable carrier. These topical formulations are in the form of conventional salves, lotions, sprays, powders and the like, well known in the pharmaceutical art.

The present invention is illustrated by the following examples. However, it should be understood that the invention is not limited to the specific details of these examples. Nuclear magnetic resonance spectra were recorded on a Bruker ($^1$HNMR, 250 MHz; $^{13}$CNMR, 62.8 MHz) or a Varian ($^1$HNMR, 300 MHz; $^{13}$CNMR, 75 MHz) spectrometer. The carbon type (methine, methylene, methyl or quaternary) was determined by DEPT experiments. Mass spectra were recorded on an AEI MS-30 spectrometer equipped with a D5-50 data system.

EXAMPLE 1

4″-0-Acetyl-12,12′-anhydro-9-deoxo-11-deoxy-9R,11-(thiocarbonyldioxy)erythromycin A (3a)

To a mechanically stirred ethyl acetate solution (1.5L) of the title product of Preparation 1 (4a; 122 g, 0.14 mol) and triethylamine (537 ml, 3.9 mol), which was maintained at −1° C., was rapidly added thionyl chloride (10 ml, 0.13 mol), such that the reaction temperature did not exceed +7° C. After the thionyl chloride addition was complete, the reaction mixture was stirred for 10 minutes and TLC [silica(impregnated with formamide)/CHCl$_3$ and silica/CHCl$_3$/MeOH/NH$_3$ (9:1:0.1)] indicated starting material and one, major new material (ca. 1:1 ratio). Additional thionyl chloride (5 ml, 0.065 mol) was added, again, the reaction temperature was never allowed to surpass +7° C., and, after stirring for 15 minutes, TLC [silica(impregnated with formamide)/CHCl$_3$] indicated starting material and one, major new material (ca. 1:2 ratio). A final addition of thionyl chloride (2 ml, 0.026 mol) was made and, after stirring at +7° C. for 15 minutes, TLC [silica(impregnated with formamide)/CHCl$_3$]indicated a starting material to product ratio of about 1:9. After stirring an additional 30 minutes at +7° C., the reaction was poured into a stirring mixture of ethyl acetate/water (250 ml/1L) and the pH was adjusted to 9.6. The organic layer was separated, washed with water (3×500 ml), treated with Darco, dried over anhydrous sodium sulfate, and concentrated in vacuo, affording a yellow solid (130 g). The solid was crystallized from isopropanol/water to afford colorless crystalline title product (3a), 62 g; mp 249–252° C.; $^1$HNMR (CDCl$_3$) delta 0.85–1.30 (m), 1.50–1.80(m), 1.95(s), 2.00(s), 2.25(s), 2.27–2.80(m), 3.29(s), 3.55(brd), 3.71(s), 3.80(m), 3.95(brd), 4.10(brs), 4.15(m), 4.35(d), 4.60(d), 4.80(m), 4.95(brs), 5.25(s), 5.51(s), 5.55(d); $^{13}$CNMR (CDCl$_3$) delta 190.4 (CS), 174.8(lactone), 169.6(acetyl), 138.5(Q), 116.4(CH$_2$), 99.4(CH), 94.7(CH), 91.6(CH), 82.8(CH), 77.9(CH), 77.7(CH), 76.8(CH), 75.8(CH), 73.5(Q), 72.8(Q), 71.2(CH), 68.1(CH), 63.5(CH) 62.8(CH), 48.8(CH3), 43.9(CH), 42.5(CH), 40.5[2(CH$_3$)], 38.4(CH$_2$), 34.5(CH$_2$), 32.5(CH), 31.0(CH$_2$), 30.5(CH), 29.0(CH$_2$), 21.8(CH$_3$), 21.31(CH$_3$), 21.0(CH$_3$), 20.6(CH$_3$), 17.3(CH$_3$), 16.8(CH$_3$), 14.2(CH$_3$), 11.3(CH$_3$), 10.6(CH$_3$), 9.2(CH$_3$).

Anal. Calcd for C$_{42}$H$_{69}$O$_{14}$NS: C, 59.76; H, 8.24; N, 1.66, S, 3.80. Found: C, 59.55; H, 8.09; N, 1.63; S, 3.69.

The same product is obtained by the same method from the title product of Preparation 2.

EXAMPLE 2

4″-O-Acetyl-12,12′anhydro-9-deoxo-9R-hydroxyerythromycin A (3b)

To a mechanically stirred isopropanol (500 ml) suspension of the title product of the preceding Example (3a; 50.0 g, 59 mmol) was added in a portionwise fashion sodium borohydride (5.0 g, 132 mmol), and the resulting mixture was allowed to stir at room temperature overnight. After this period, TLC [silica/CHCl$_3$/MeOH/NH$_3$ (9:1:0.1)] indicated no remaining starting and one, more polar material. The reaction mixture was then poured into a stirring mixture of methylene chloride/water (2.0L/2.5L) and the organic layer was separated, washed with aqueous saturated sodium chloride (3×400 ml), dried over anhydrous sodium sulfate, and concentrated in vacuo affording a colorless solid (25 g). The aqueous fractions were combined and continuously extracted with chloroform affording, after concentration, a pale yellow solid (13 g). These materials were combined (38 g) and refluxed in methanol (250 ml) for 4 hours. After this period, TLC [silica/CHCl$_3$/MeOH/NH$_3$ (9:1:0.1)] indicated essentially no starting material and mostly (ca. 90%) one, more polar material. The reaction mixture was allowed to cool to room temperature and concentrated in vacuo affording a pale yellow solid (40 g). The solid was allowed to dissolve in a stirring mixture of tetrahydrofuran/bleach (50 ml/50 ml) and allowed to stir at 0° C. for 5 minutes, at which time the tetrahydrofuran was removed in vacuo. The resulting solution was added to a stirring mixture of methylene chloride/water (250 ml/200 ml), phase separated, and the aqueous layer was reextracted with fresh methylene chloride (250 ml). The combined organic layers were washed with aqueous saturated sodium chloride (2×75 ml), dried over anhydrous sodium sulfate and concentrated in vacuo affording a colorless solid (33 g). The solid was added to a stirring mixture of methylene chloride/water (170 ml/170 ml) and the pH was adjusted to 5.1 (6N HCl). After phase separation, fresh methylene chloride (150 ml) was added and the pH adjusted to 6.1 (6N HCl). The methylene chloride extracts were combined, added to water (500 ml), pH adjusted to 9.5 (6N NaOH), phase separated, dried over anhydrous sodium sulfate and concentrated in vacuo affording present title product (3a) as a colorless solid, 27 g; $^{13}$CNMR (CDCl$_3$) delta 175.0 (lactone) 165.8 (acetyl), 146.3(Q), 115.2 (CH$_2$), 102.0(CH), 95.1(CH), 84.5(CH), 81.1(CH), 79.2(CH), 78.0(CH), 76.8(CH), 74.4(Q), 72.6(Q), 70.5(CH), 69.4(CH), 68.6(CH), 64.9(CH), 63.3(CH), 49.0($CH_3$), 43.5(CH), 43.3(CH), 40.1[2($CH_3$)], 39.4($CH_2$), 34.8($CH_2$), 34.8(CH), 34.0(CH), 29.0($CH_2$), 27.7($CH_2$), 21.8($CH_3$), 21.2($CH_3$), 21.1($CH_3$), 20.5($CH_3$), 19.3($CH_3$), 17.0($CH_3$), 13.2($CH_3$), 11.8($CH_3$), 10.4($CH_3$), 9.6($CH_3$)

EXAMPLE 3

4''-O-Acetyl-9-deoxo-9R-12'-dihydroxyerythromycin A(3d)

A mechanically stirred solution of the title product of the preceding Example (3b; 20.0 g, 26.2 mmol) in tetrahydrofuran/water (360 ml/40 ml) was adjusted to pH 6.1 (3N HCl) and osmium tetroxide/ t-butyl alcohol (2.5% solution, 40 ml, 3.9 mmol) was added at room temperature. After stirring the dark amber solution at room temperature for 1 hour, sodium metaperiodate (11.2 g, 52.4 mmol) was added and the resulting mixture was stirred at room temperature for 22 hours. After this period, TLC [silica/$CH_2Cl_2$/MeOH/$NH_3$ (9:1:0.1)] indicated little starting material (ca. 10%) and essentially one, more polar material. Tetrahydrofuran (100 ml) and aqueous sodium sulfite (1M, 220 ml) were added and the mixture stirred at room temperature for 15 minutes. The reaction mixture was then poured into a stirring mixture of methylene chloride/water (800 ml/1400 ml), phase separated, the aqueous reextracted with methylene chloride (3×400 ml), dried over anhydrous sodium sulfate and concentrated in vacuo affording an amber solid (19.1 g). The solid was added to a stirring mixture of methylene chloride/water (100/100 ml) and the pH adjusted to 2.6, phase separated, the pH of the aqueous phase was readjusted to 4.8 and extracted with methylene chloride (2×150 ml), phase separated and the pH of the aqueous phase was finally adjusted to 9.5 and extracted with methylene chloride (3×200 ml). The methylene chloride extracts at pH 9.5 contained no starting material [TLC/silica/$CH_2Cl_2$/MeOH/$NH_3$ (9:1:0.1)] and upon drying over anhydrous sodium sulfate and concentration in vacuo afforded a colorless solid (14 g). The solid was dissolved in chloroform (60 ml) and allowed to stand at room temperature for 15 minutes, affording a thick crystalline mass. At this point hexane (180 ml) was added with vigorous stirring and the resulting slurry was stirred at room temperature overnight, which afforded, after filtration, colorless, crystalline title product (3d), 11 g; mp 148–151° C.; $^1$HNMR (CDCl$_3$) delta 0.79(t), 0.95–1.20(m), 1.45–1.90(m), 1.99(s), 2.25(s), 2.35–2.70(m), 3.22(s), 3.40(brm), 3.55(dd), 3.65(s), 3.70(m), 3.85(s), 3.95(d), 4.25(m), 4.59(dd), 4.91(d), 5.05(dd); $^{13}$CNMR (CDCl$_3$) delta 176.2(lactone), 170.4(lactone), 101.5(CH), 95.4(CH), 83.0(CH), 82.7(CH), 78.3(CH), 78.1(CH), 77.5(CH), 75.5(Q), 74.6(Q), 72.5(Q), 70.9(CH), 69.2(CH), 68.1(CH), 64.1(CH), 63.2(CH), 61.9($CH_2$), 49.0($CH_3$), 44.3(CH), 41.9(CH), 40.1[2($CH_3$)], 36.4($CH_2$), 34.7($CH_2$), 34.3(CH), 32.0(CH), 29.5($CH_2$), 23.7($CH_3$), 22.1($CH_2$), 21.1($CH_3$), 21.0($CH_3$), 20.5($CH_3$), 19.4($CH_3$), 17.3($CH_3$), 15.1($CH_3$), 13.7($CH_3$), 11.0($CH_3$), 9.1 ($CH_3$); High resolution mass spectrum m/e 635.3554 (P-desosamine, $C_{31}H_{55}O_{13}$), 592.3720 (P-4''-acetyl cladinose-beta-cleavage, $C_{29}H_{54}NO_{11}$), 576.3687 (P-4''-acetyl cladinose, $C_{29}H_{54}NO_{10}$), 434.2814 (aglycon, $C_{21}H_{38}O_9$), 201.1104 (4''-acetyl cladinose, $C_{10}H_{17}O_4$), 158.1158(desosamine, $C_8H_{16}NO_2$).

Anal. Calcd for $C_{39}H_{71}O_{15}N$: C, 58.99; H, 8.95; N, 1.76. Found: C, 58.77; H, 8.83; N, 1.72.

The structure of the present compound was confirmed by X-ray crystallographic analysis of its 2'-benzoate derivative, prepared by benzoylation of the title compound according to Preparation 2.

EXAMPLE 4

12,12'-Anhydro-9-deoxo-9R-hydroxyerythromycin A(3c)

The title product of Example 2 (2 g) is combined with 50 ml of conc. $NH_4OH$ and 50 ml of methanol and stirred for 18 hours. The mixture is then poured into 100 ml of water, saturated with NaCl and extracted 3×200 ml $CH_2Cl_2$. The organic extracts are combined, dried over $Na_2SO_4$ and stripped in vacuo to yield present title product.

The same method applied to the title product of Example 1 produces the same product.

EXAMPLE 5

9-Deoxo-9R,12'-dihydroxyerythromycin A(3e)

The title product of Example 3 (200 mg) is dissolved in 20 ml dioxane. LiOH (20 mg) and then 5 ml $H_2O$ are then added and the mixture stirred for 18 hours, then poured into 50 ml of $H_2O$ and 50 ml of $CH_2Cl_2$. The aqueous phase is separated and extracted with 50 ml fresh $CH_2Cl_2$. The organic layers are combined, dried over $Na_2SO_4$ and stripped in vacuo to yield present title product.

PREPARATION 1

2',4''-Di(O-acetyl)-9-deoxo-11-deoxy-9R,11-(thiocarbonyldioxy)erythromycin A(4a)

To a methylene chloride solution (2.7L) of a 9-deoxo-111-deoxy-9R,11-(thiocarbonyldioxy)erythromycin A, 2; 290.0 g, 0.37 mol) containing triethylamine (171 ml, 1.2 mol) and dimethylamino pyridine (10.7 g, 0.09 mol) was added, in a dropwise fashion, acetic anhydride (99 ml, 1.0 mol), such that the reaction temperature never exceeded 30° C. After the resulting solution was stirred overnight, TLC [silica/$CHCl_3$/MeOH/$NH_3$ (9:1:0.1)] indicated no remaining starting 2 and one, less polar UV positive material. Water (1 L) was then added and the pH was adjusted to 9.6 (6N NaOH). The organic layer was separated, washed with water (3×500 ml) and aqueous saturated sodium chloride (1×500 ml), dried over anhydrous sodium sulfate, and concentrated in vacuo. The resulting yellowish solid was crystallized from hot diethylether (1.5 L), affording colorless, crystalline 3 (260 g). High resolution mass spectral analysis supported bisacetate formation, m/e 200.1280 (2'-acetyl desosamine, $C_{10}H_{18}NO_3$), 201.1110 (4''-acetyl cladinose, $C_{10}H_{17}O_4$).

PREPARATION 2

4''-O-Acetyl-2'-O-benzoyl-9-deoxo-11-deoxy-9R,11-(thiocarbonyldioxy)erythromycin A(4b)

Substituting 1 molar equivalent of either benzoic anhydride or benzoyl chloride for the excess acetic anhydride of the preceding Example, the same starting material (2) was converted to crystalline 2'-O-benzoyl11-deoxy-9R,11-(thiocarbonyldioxy)erythromycin used in X-ray crystal structure studies. By the method of Preparation 1, that monoester is further converted to present title product (4b).

I claim:
1. A compound of the absolute stereochemical formula

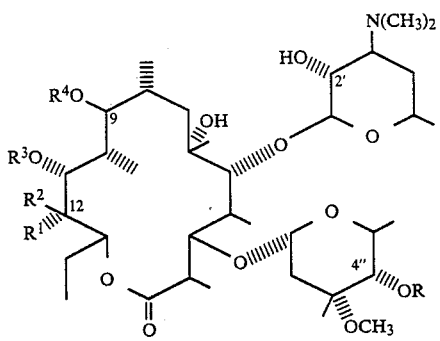

wherein
R is hydrogen or (C$_2$-C$_4$) alkanoyl;
R$^1$ and R$^2$ are taken separately, R$^1$ is hydroxymethyl and R$^2$ is hydroxy; or
R$^1$ and R$^2$ are taken together and are methylene; and
R$^3$ and R$^4$ are taken separately and are each hydrogen; or
R$^3$ and R$^4$ are taken together and are thiocarbonyl; with the proviso that when R$^3$ and R$^4$ are so taken, R is other than hydrogen;
or a pharmaceutically acceptable acid addition salt thereof.
2. A compound of claim 1 wherein R is acetyl.
3. A compound of claim 2 wherein R$^1$ and R$^2$ are taken together and are methylene.
4. The compound of claim 3 wherein R$^3$ and R$^4$ are taken together and are thiocarbonyl.
5. A compound of claim 2 wherein R$^3$ and R$^4$ are taken separately and are each hydrogen.
6. The compound of claim 3 wherein R$^3$ and R$^4$ are taken separately and are each hydrogen.
7. The compound of claim 5 wherein R$^1$ is hydroxymethyl and R$^2$ is hydroxy.
8. A compound of the absolute stereochemical formula

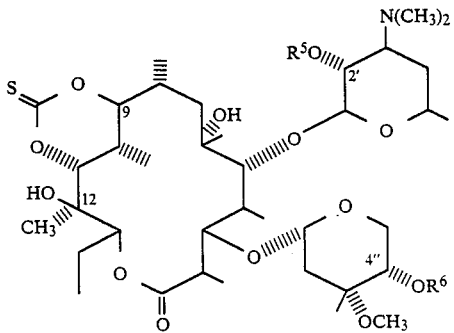

wherein R$^5$ is (C$_2$-C$_4$) alkanoyl or benzoyl; and R$^6$ is (C$_2$-C$_4$) alkanoyl.
9. The compound of claim 8 wherein R$^5$ and R$^6$ are each acetyl.
10. The compound of claim 8 wherein R$^5$ is benzoyl and R$^6$ is acetyl.

* * * * *